United States Patent
Worthington

(10) Patent No.: US 7,506,647 B2
(45) Date of Patent: Mar. 24, 2009

(54) TRACHEOSTOMA CANNULA MOUNTING

(75) Inventor: Ian David Worthington, Wetherby (GB)

(73) Assignee: Kapitex Healthcare Limited, West Yorkshire (GB)

( * ) Notice: Subject to any disclaimer, the term of this patent is extended or adjusted under 35 U.S.C. 154(b) by 347 days.

(21) Appl. No.: 10/519,997

(22) PCT Filed: Jun. 9, 2003

(86) PCT No.: PCT/GB03/02473

§ 371 (c)(1),
(2), (4) Date: Aug. 16, 2005

(87) PCT Pub. No.: WO2004/004816

PCT Pub. Date: Jan. 15, 2004

(65) Prior Publication Data

US 2007/0079831 A1    Apr. 12, 2007

(30) Foreign Application Priority Data

Jul. 6, 2002   (GB) ................... 0215733.7

(51) Int. Cl.
*A61M 16/00*    (2006.01)
(52) U.S. Cl. ................. 128/207.14; 128/207.16; 128/207.17
(58) Field of Classification Search ........... 128/207.14, 128/207.29, 207.15, 207.16, 207.17; 604/174
See application file for complete search history.

(56) References Cited

U.S. PATENT DOCUMENTS

| 3,640,741 | A | * | 2/1972 | Etes | 106/194.2 |
| 4,711,237 | A | * | 12/1987 | Kaiser | 128/859 |
| 5,000,741 | A | * | 3/1991 | Kalt | 604/180 |
| 5,464,011 | A | * | 11/1995 | Bridge | 128/207.14 |
| 5,819,734 | A | * | 10/1998 | Deily et al. | 128/207.17 |
| 5,918,599 | A | * | 7/1999 | Shesol | 128/207.17 |
| 6,668,831 | B1 | * | 12/2003 | Hegwood | 128/207.14 |
| 6,701,928 | B2 | * | 3/2004 | Rubin et al. | 128/207.14 |
| 6,772,758 | B2 | * | 8/2004 | Lambert | 128/204.17 |
| 6,998,511 | B2 | * | 2/2006 | Worthley | 602/57 |

FOREIGN PATENT DOCUMENTS

EP    0 081 907 A1    6/1983
EP    0 387 220 B1    9/1990

* cited by examiner

*Primary Examiner*—Steven O Douglas
(74) *Attorney, Agent, or Firm*—Sughrue Mion, PLLC

(57) ABSTRACT

A tracheostoma cannula mounting, a cannula assembly incorporating such a mounting, and a method of mounting the same within a stoma are described. The mounting includes a generally planar sheet portion (2) provided with an aperture (4) therein of suitable size and shape to engage a channel portion of a tracheostoma cannula (21) in interference fit so as to present a rearward mounting face (18) adapted in use to lie against the skin of the tracheostoma patient in the vicinity of the stoma. The material from which the sheet (2) is fabricated comprises tacky gel material such as silicone gel at least in the vicinity of the mounting face (18), and is preferably made essentially entirely from such material.

12 Claims, 3 Drawing Sheets

TRACHEOSTOMA CANNULA MOUNTING

This is a National Stage of Application No. PCT/GB2003/002473 filed Jun. 9, 2003.

The invention relates to a tracheostoma cannula mounting for mounting of a cannula through a tracheostoma in patients who have received a tracheostomy, for example as part of a laryngectomy. In particular, the mounting is intended to provide a gas tight seal between the cannula and the stoma, so that air is inhaled and exhaled through the cannula tube only and does not escape around the edges of the stoma.

A tracheostomy is a surgical procedure in which an opening is formed through the anterior surface of the neck into the trachea. The opening is referred to as a tracheostoma. A cannula can be provided for insertion into the stoma to keep the stoma open and provide a breathing air passage, and this can extend through the tracheostoma and into the trachea. The cannula can also be used to provide for attachment of various devices, including filters, stoma valves, vocal prosthesis devices and the like, at either its forward or its tracheal opening.

For example, a heat-moisture-exchange filter may be so fitted. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled airstream, and the action of cilia transports mucous and any particles away from the lungs.

However, when a patient has received a laryngectomy, the trachea is no longer connected to the pharynx but is diverted to the tracheostoma. All inhaled air enters the lungs by the tracheostoma, and the nose and upper part of the respiratory tract above the stoma are effectively not involved the inhalation process. For this reason, it is often desirable to fit heat and moisture exchange filters to a laryngectomy patient. These can conveniently be fitted to an outer end of the cannula in the stoma.

Similarly, a phonation valve may be so fitted. A further consequence of a laryngectomy is that speech is no longer available by the normal method of passage of air through the vocal cords of the larynx. Where clinical conditions permit, it is clearly in the patient's interest to restore the facility of speech. It is sometimes possible to insert a voice prosthesis in an artificially created fistula between the upper region of the trachea and the oesophagus. It then becomes necessary to provide means for directing the flow of exhaled air through the voice prosthesis. This can be conveniently achieved by the incorporation of a valve in an externally worn device to selectively close the stoma. Again, such a device can conveniently be fitted to the outer end of a cannula in the stoma.

It can be seen for all of these applications in particular a cannula can be useful. It is generally desirable that the cannula is mounted within the stoma in a generally air tight manner, so that during inhalation and exhalation air merely passes through the breathing passage provided the inside of the cannula, and does not leak through gaps between the outer surface of the cannula and the stoma.

Typical prior art tracheostoma cannulas are fabricated from suitable medical grade material, and in a conventional design have a generally cylindrical central channel portion adapted to sit within the stoma to provide an air passage therethrough into the trachea, a forward section provided with a mounting for a stoma filter, valve or the like, and a rearward mounting section comprising an area of greater cross section, for example in the form of a resilient flange, which sits within the trachea and bears onto the tracheal surface to retain the cannula within the stoma. Such devices are fabricated of material having a degree of flexible resilience, for example medical grade silicone rubber. This assists in insertion and removal. The resilient nature of the material assists in effecting a reasonable seal between the edges of the stoma and the outer face of the central portion of the cannula, but the seal is not always perfect.

In problem patients, it has in consequence sometimes proved necessary to apply an additional seal in the form of an adhesive material between the skin around the stoma in the tracheal regions and the central portion of the cannula for example comprising medical adhesive fabric sheet or tape. Such as solution is not ideal. Any such adhesive sheet or tape would need frequent changing for hygiene purposes and the used sheet or tape would then need to be discarded. The adhesive is likely to cause irritation to sensitive skin at and around the stoma, especially in patients with a sensitive or allergic reaction to generally used adhesive materials.

It is an object of the present invention to provide a mounting for a tracheostoma cannula which provides a more effective air seal between the cannula and the stoma than is provided by conventional resilient cannula materials alone.

It is a further object of the present invention to provide a mounting for a tracheostoma cannula which mitigates some of the disadvantages of mountings based on adhesive sheet or tape.

It is a particular object of the present invention to provide a releasable removable mounting which can be removed for cleaning and subsequently reused.

Thus, in accordance with the invention in its broadest concept there is provided a tracheostoma cannula mounting for assisting in the mounting of a cannula within a stoma of a tracheostoma patient comprising a generally planar sheet portion provided with an aperture therein of suitable size and shape to engage a channel portion of a tracheostoma cannula in interference fit so as to present a rearward mounting face adapted in use to lie against the skin of the tracheostoma patient in the vicinity of the stoma, wherein the material from which the sheet is fabricated comprises tacky gel material at least in the vicinity of the mounting face.

The mount is thus engaged over the central channel portion of the cannula in interference fit so as to sit therearound externally of the stoma but in contact with the skin surface of the patient. The mounting surface in such contact comprises tacky gel material which therefore is inherently adhesive, and effects a good air tight seal even with a relatively rough skin surface. A much improved seal is thereby achieved between cannula and stoma. This is assisted in that the gel of the sheet portion is also inherently mouldable to the shape of the user's neck.

The seal is much more effective than would be provided by the resilience of the cannula alone. The seal also offers significant advantages over seals comprising applied adhesive sheet or tape or the like. The gel material is tacky because of its inherent properties. As a result, the mounting can be removed for washing, and will retain its tackiness at least for a limited repeated reuse.

A mounting member in accordance with the invention is simple and cheap to produce, but offers an effective, hygienic and convenient solution to the problem of providing a more effective seal between the outer surface of a cannula of conventional design and the edge of a stoma than prior art solutions, which has the advantage of being reusable.

The mounting comprises a sheet portion which is itself composed of tacky gel material at least in the vicinity of the mounting face. This tacky gel material can be a tacky gel layer in a multi-layer sheet, other layers providing further properties, e.g. to give desired mechanical robustness and resilience. However, for simplicity, a single layer structure is preferred with the gel material suitably selected for such other properties, for example having adequate mechanical strength.

Conveniently therefore, the sheet portion of the mounting member consists essentially solely of the tacky gel material. In particular, the inner edge defining the aperture in the mounting member conveniently presents a surface of such tacky material in contact with the cannula. This assists in provision of an effective air seal. Edges and/or faces of the sheet portion which are adapted to lie externally in use may nevertheless preferably be provided with a thin layer of non-tacky protective material, for example in the form of a suitable thin flexible cover sheet of suitable polymeric or other material.

The aperture in the sheet portion of the mounting member is shaped and sized to match the outer circumference of the channel portion of the cannula. Cannulas of conventional design will generally have a cylindrical body portion adapted to be passed through a generally circular stoma. Accordingly, the aperture in the sheet portion of the mounting member will conveniently similarly be circular. The mounting member itself may be of any suitable shape. In many instances it will be preferable also that an outer edge of the mounting member is generally circular, such that the mounting member comprises an annular portion of sheet material.

The sheet material is of suitable thickness for the application envisaged, conveniently being 1 to 7 mm thick. Sheet portions are conveniently cut from a large sheet of such material, optionally already provided with protective and/or backing layers as above described, for example by press cutting. The mounting member is thus easily mass produced from simply fabricated base materials.

Prior to use the mounting surface of the mounting member may be protected by provision of a removable non-tacky protective layer which can readily be removed by a user to expose the tacky surface of the gel to allow the mounting member to be applied. For example, a removable backing sheet of a design familiar from that used with conventional adhesive sheet or tape will be suitable.

The material for the sheet portion may be any suitable gel material where the degree of cross-linking is sufficiently controlled to give a degree of tackiness to the surface, and hence the necessary adhesion in use. Particularly suitable materials include silicone gels. These exhibit many of the desirable properties, do not generally cause irritation to the skin in the majority of patients, and should generally operate well with the silicone rubbers typically used for stoma cannulas.

In a further aspect of the invention there is provided a tracheostoma cannula comprising a central channel portion, in particular a cylindrical central channel portion, adapted to be received through a stoma, a forward portion adapted to sit externally of the stoma in use, and in particular provided with means for mounting filters, valves or the like, and a mounting portion adapted to sit within the trachea abutting an internal surface of the stoma in use, and comprising a flange portion of increased cross section to the body portion so as to assist in retaining the cannula within the stoma, and in particular in retaining and sealing the cannula in the stoma, and further comprising a mounting as above described, comprising a sheet portion provided with an aperture so sized and shaped as in use to be retained around the channel portion of the cannula immediately external of the stoma in interference fit, so as to present a mounting face to the external surface of the tracheal region of the wearer in the vicinity of the stoma, wherein the material from which the sheet portion is fabricated comprises tacky gel material at least in the vicinity of the mounting face.

In a further aspect of the invention, a kit of parts for mounting a tracheostoma cannula comprises a suitable cannula, in particular comprising a central channel portion, forward portion and rearward mounting portion as above described, at least one cannula mounting in accordance with the first aspect of the invention, and optionally filters, valves etc. for mounting on the forward portion of the cannula.

In a further aspect of the invention a method of sealably mounting a cannula in a tracheostoma comprises use of a mounting in accordance with the first aspect of the invention, in particular by the steps of inserting a cannula into the stoma, applying the mounting therearound so as to present the mounting face to the skin in the vicinity of the stoma, applying pressure to effect a releasable seal between mounting face and skin.

The invention will now be described by way of example only with reference to FIGS. 1 to 3 of the accompanying drawings in which:

FIG. 1 illustrates an embodiment of a mounting member in accordance with the invention shown in plan view in FIG. 1a and as a vertical section (through A-A on FIG. 1a) in FIG. 1b.

The mounting member comprises an annular sheet portion (2) stamped from a sheet of suitable tacky gel material. In the embodiment, a medium viscosity silicone gel is used, specifically being MED-6345 from NuSil Silicone Technology. An aperture (4) is provided in the sealing member, suitable sized and shaped relative to the main body portion of a cannula about which the sealing member is designed to engage so as to be mountable thereon with a snug interference fit. The tacky exposed inner surface (5) of the aperture (4) assist in the creation of an air tight seal between the sealing member and the body portion of the cannula.

Figure 1A:
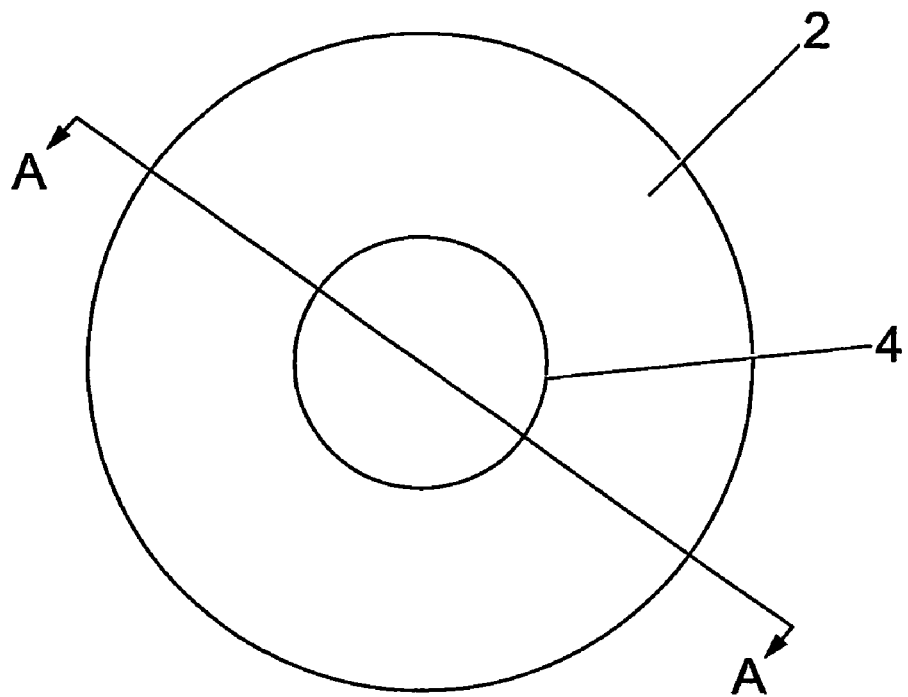
FIGS. 1A and 1B are top and cross-sectional views, respectively, of a sealing member in accordance with the invention.
Figure 1B:
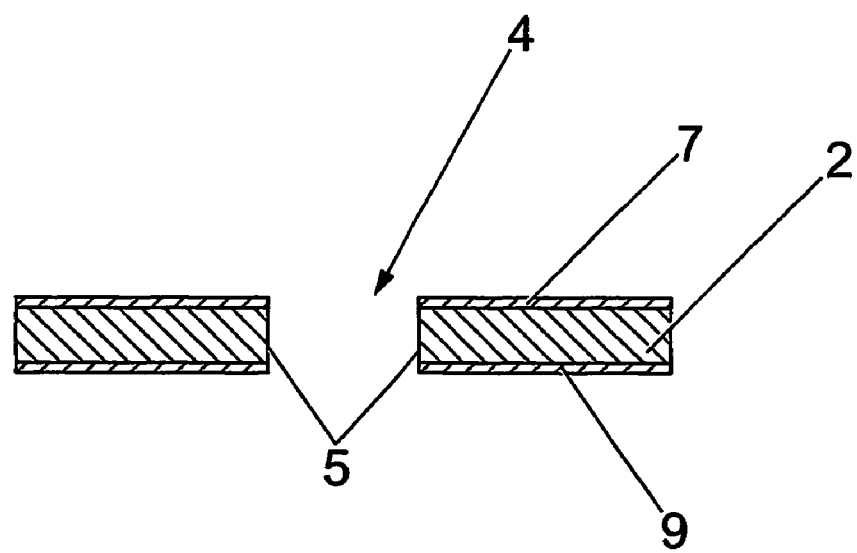

A cross-section through A-A of FIG. 1a is shown in FIG. 1b. As FIG. 1b illustrates, the annular gel portion (2) is provided with two surface coverings. The first is a permanently bonded polymeric sheet cover (7), situated on what is intended to be in use the outer surface, to protect an prevent accumulation of debris on the outer surface in use. The second is a temporary peelable backing sheet (9) intended to protect the rear, bonding surface of the gel (2) before use. The sheet (9) is not permanently bonded to the gel (2), but is releasably attached thereto, for example making use of the inherent tackiness of the gel, to allow it to be peeled away when the device is to be used and expose the mounting surface.

Figure 2:
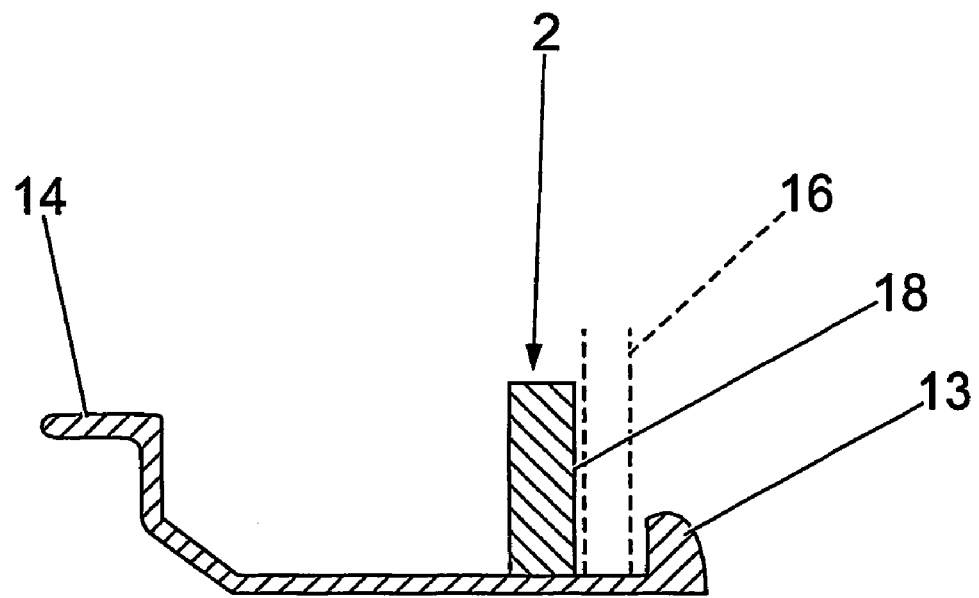
FIG. 2 is an illustration of the sealing member of FIG. 1 mounted upon a self retaining cannula of conventional design.
Figure 2:
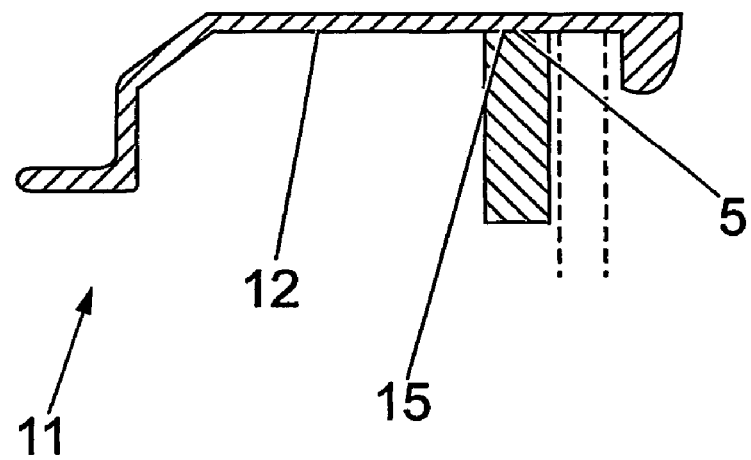

The embodiment of FIG. 1 is shown in position on a cannula of a stoma stud of conventional design in cross section in FIG. 2. The cannula of the stoma stud is of typical self retaining design. The cannula (11) comprises a one piece construction of silicone rubber comprising three basic components. A cylindrical central portion (12) fits through the stoma in use (the position of the tracheal wall being shown by the broken line (16)). The cannula is held in place by a rearward flanged mounting portion (13). A forward portion (14) of the cannula is adapted to receive a suitable attachment, such as a heat moisture exchange or other filter, a valve, or some combination thereof. Suitable conventional attachments will readily suggest themselves to the skilled person.

In use, the backing sheet (9) is removed from the sealing member (2) to expose the mounting face (18). The sealing member (2) is located into position around the body portion (12) of the cannular. It is retained there in part by and interference fit effected by the resilience of the material of the sealing member (2), but the seal between a face (15) of a cannula body portion (12) and a face (5) of the sealing member (2) is made more effective by the tacky action of the gel. Pressure is applied to push the mounting member onto the skin surface of the tracheal region of the user in the vicinity of the stoma so that the mounting face (18) of the mounting member (2) effects a releasable air tight seal with the skin.

Figure 3:
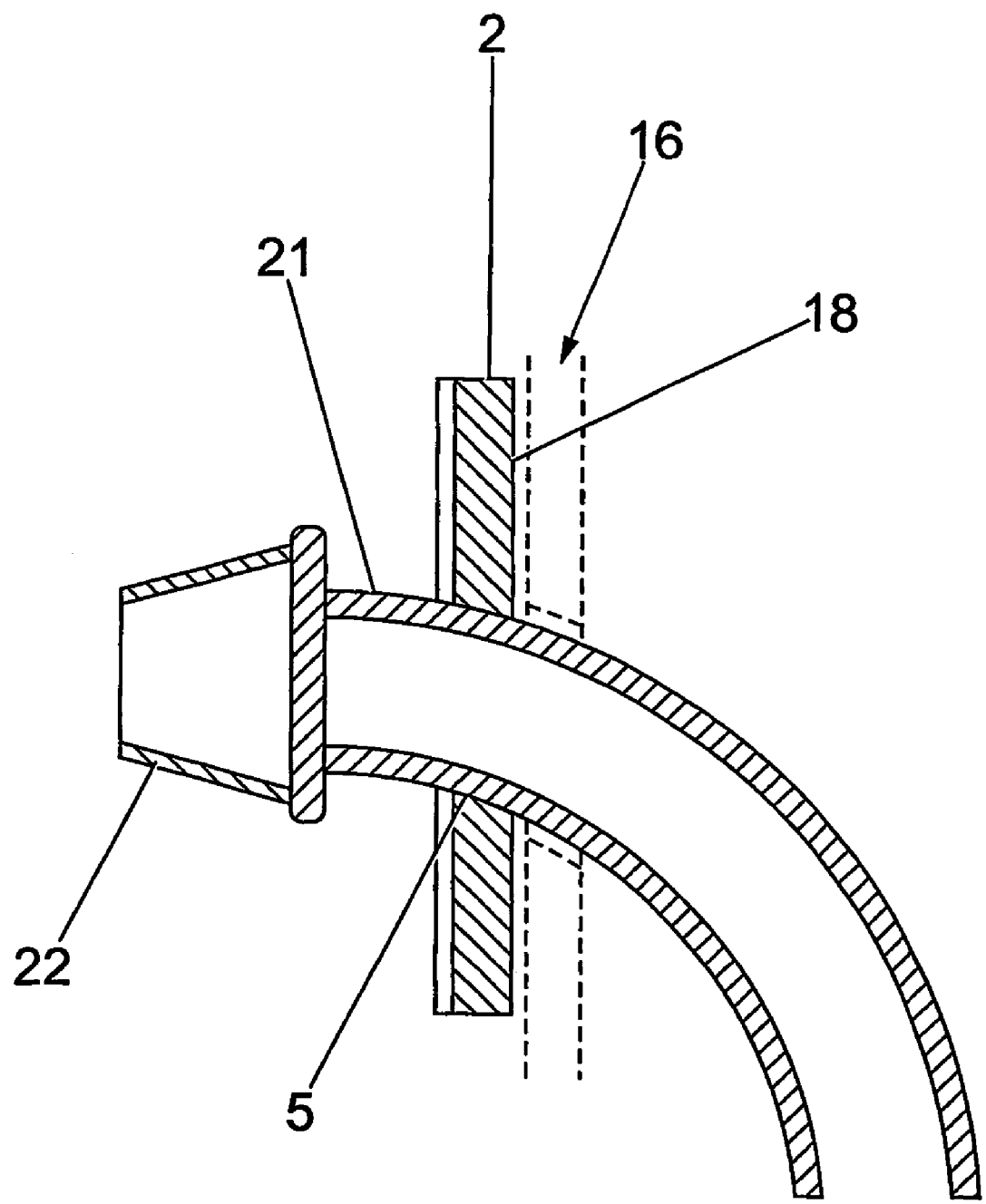
FIG. 3 is an illustration of the sealing member of FIG. 1 mounted upon a cannula of alternative conventional design.

FIG. 3 shows a cross-section of a conventional shaped cannula, of the sort usually requiring a retaining strap (not shown), typically serving as a tracheostomy tube, with the seal of FIG. 1 shown in position.

The embodiment shown in the Figures is very easy to apply to form an effective air tight seal in conjunction with a tracheostoma cannula. It is cheap and simple to manufacture. It is convenient and hygienic to use, in that it can be readily removed to be washed and then reused, since its adhesion to the patient depends on the inherent properties of the gel (2) rather than on any additional adhesive layer. The materials selected are generally well tolerated by a patient.

A tube (21) is provided with a valve closure of conventional design (22) at a distal end and passes through the stoma in the tracheal wall (broken line 16) into the trachea. A seal is effected by application of a sealing member (2) around the tube (21). Again, a mounting face (18) effects a seal on the skin in the tracheal region and an annular face (5) seals with the tube (21) by a combination of interference fit and gel adhesion.

The invention claimed is:

1. A tracheostoma cannula mounting member for assisting in the mounting of a tracheostoma cannula within a stoma of a tracheostoma patient comprising a generally planar sheet portion provided with an aperture therein of suitable size and shape that engages a channel portion of the tracheostoma cannula in an interference fit so as to present a rearward mounting face adapted in use to lie against skin of the tracheostoma patient in the vicinity of the stoma, wherein material from which the sheet is fabricated comprises tacky gel material at least in the vicinity of the mounting face.

2. A tracheostoma cannula mounting in accordance with claim 1 wherein an inner edge defining the aperture in the mounting member presents a surface of tacky gel material to contact with the cannula in use.

3. A tracheostoma cannula mounting in accordance with claim 1 wherein the sheet portion comprises a tacky gel layer in a multi-layer sheet.

4. A tracheostoma cannula mounting in accordance with claim 1 wherein the sheet portion consists essentially of the tacky gel material.

5. A tracheostoma cannula mounting in accordance with claim 1 wherein the aperture in the sheet portion of the mounting member is generally circular and shaped and sized to engage the outer circumference of the channel portion of the cannula in the interference fit, and wherein the channel portion is cylindrical.

6. A tracheostoma cannula mounting in accordance with claim 5 wherein the mounting member is generally circular, such that the mounting member comprises an annular portion of sheet material.

7. A tracheostoma cannula mounting in accordance with claim 1 wherein the sheet material is 1 to 7 mm thick.

8. A tracheostoma cannula mounting in accordance with claim 1 further comprising a removable non-tacky protective layer over the mounting face which can readily be removed by a user to expose a tacky surface of the gel to allow the mounting member to be applied.

9. A tracheostoma cannula comprising a central channel portion adapted to be received through a stoma, a forward portion adapted to sit externally of the stoma in use and a mounting portion adapted to sit within a trachea abutting an internal surface of the stoma in use, and comprising a flange portion of increased cross section to a body portion so as to assist in retaining the cannula within the stoma, and further comprising a mounting comprising a generally planar sheet portion provided with an aperture therein so sized and shaped to be retained around the channel portion of the cannula immediately external of the stoma in interference fit, so as to present a mounting face engageable upon an external surface of a tracheal region of a wearer in the vicinity of the stoma in use, wherein material from which the planar sheet portion is fabricated comprises tacky gel material at least in the vicinity of the mounting face.

10. A method of sealably mounting a tracheostoma cannula mounting comprising a generally planar sheet portion provided with an aperture therein of suitable size and shape that engages a channel portion of a tracheostoma cannula in an interference fit so as to present a rearward mounting face adapted in use to lie against skin of a tracheostoma patient in the vicinity of a stoma, wherein material from which the sheet is fabricated comprises tacky gel material at least in the vicinity of the mounting face, the method comprising: inserting a cannula into the stoma, applying the mounting around the cannula in an interference fit so as to present the rearward mounting face to skin of an external surface of a tracheal region of a wearer in the vicinity of the stoma, and applying pressure to effect a releasable seal between mounting face and skin.

11. A tracheostoma cannula mounting in accordance with claim 4, further comprising a layer of non-tacky protective material over at least one of edges and faces of the sheet portion, said layer being adapted to perform one of lying externally in use and being removed prior to use.

12. A tracheostoma cannula mounting in accordance with claim 1, wherein the tacky gel material comprises a silicone gel.

* * * * *